(12) United States Patent
Naito et al.

(10) Patent No.: US 8,274,047 B2
(45) Date of Patent: Sep. 25, 2012

(54) SUBSTRATE SURFACE INSPECTION METHOD AND INSPECTION APPARATUS

(75) Inventors: Yoshihiko Naito, Tokyo (JP); Norio Kimura, Tokyo (JP); Kenji Terao, Tokyo (JP); Masahiro Hatakeyama, Tokyo (JP); Masamitsu Itoh, Kanagawa (JP)

(73) Assignees: Ebara Corporation, Tokyo (JP); Kabushiki Kaisha Toshiba, Tokyo (JP)

( * ) Notice: Subject to any disclaimer, the term of this patent is extended or adjusted under 35 U.S.C. 154(b) by 162 days.

(21) Appl. No.: 12/537,414

(22) Filed: Aug. 7, 2009

(65) Prior Publication Data
US 2010/0032566 A1    Feb. 11, 2010

(30) Foreign Application Priority Data
Aug. 8, 2008    (JP) .................................. 2008-205097

(51) Int. Cl.
*G01N 23/00*    (2006.01)
(52) U.S. Cl. ......... 250/307; 250/306; 250/310; 250/311
(58) Field of Classification Search .................. 250/307, 250/311, 310, 306
See application file for complete search history.

(56) References Cited

U.S. PATENT DOCUMENTS

| | | | | |
|---|---|---|---|---|
| 5,583,346 A * | 12/1996 | Nakajima | ...................... | 250/587 |
| 6,172,363 B1 * | 1/2001 | Shinada et al. | ................... | 850/9 |
| 6,583,413 B1 * | 6/2003 | Shinada et al. | ................... | 850/9 |
| 6,610,980 B2 * | 8/2003 | Veneklasen et al. | ............... | 850/8 |
| 6,888,139 B2 * | 5/2005 | Tsuneta et al. | ................ | 250/311 |
| 6,954,266 B2 * | 10/2005 | Tomie | ......................... | 356/237.1 |
| 7,132,301 B1 * | 11/2006 | Fan | .................................... | 438/7 |
| 7,449,898 B2 * | 11/2008 | Honda et al. | ............. | 324/754.22 |
| 7,521,679 B2 * | 4/2009 | Nishiyama et al. | ........... | 250/310 |
| 2005/0139772 A1 * | 6/2005 | Hasegawa et al. | ............. | 250/311 |
| 2008/0237586 A1 * | 10/2008 | Sun et al. | ......................... | 257/48 |
| 2009/0194690 A1 * | 8/2009 | Nishiyama et al. | ........... | 250/307 |

FOREIGN PATENT DOCUMENTS

JP    2008-096296 A    4/2008

OTHER PUBLICATIONS

T. Liang et al., "Status and Gaps of EUV Mask Pattern Inspection Using DUV Light", Proceedings of 2007 International EUVL symposium, DI-02.

* cited by examiner

*Primary Examiner* — Jack Berman
*Assistant Examiner* — Jason McCormack
(74) *Attorney, Agent, or Firm* — Westerman, Hattori, Daniels & Adrian, LLP

(57) ABSTRACT

A substrate surface inspection method inspects for a defect on a substrate including a plurality of materials on a surface thereof. The inspection method comprises: irradiating the surface of the substrate with an electron beam, a landing energy of the electron beam set such that a contrast between at least two types of materials of the plurality of materials is within a predetermined range; detecting electrons generated by the substrate to acquire a surface image of the substrate, with a pattern formed thereon from the at least two types of materials eliminated or weakened; and detecting the defect from the acquired surface image by detecting as the defect an object image having a contrast by which the object image can be distinguished from a background image in the surface image. Defects present on the substrate surface can be detected easily and precisely by using a cell inspection.

8 Claims, 12 Drawing Sheets

[Fig. 1]
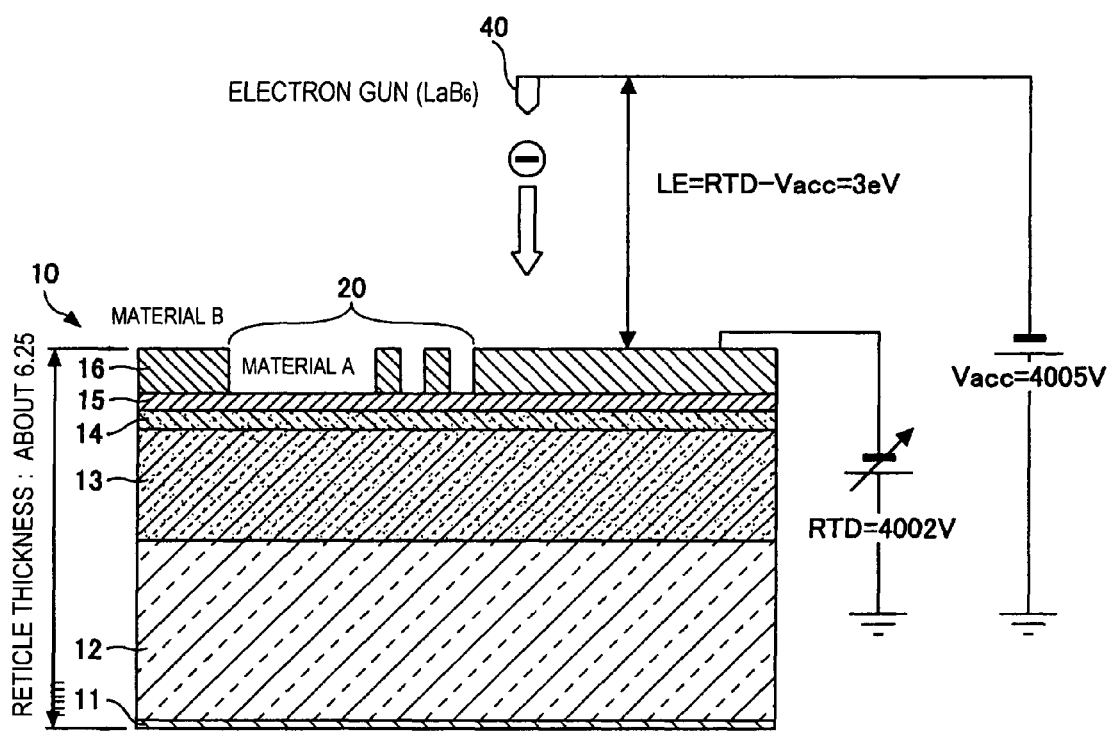

[Fig. 2A]
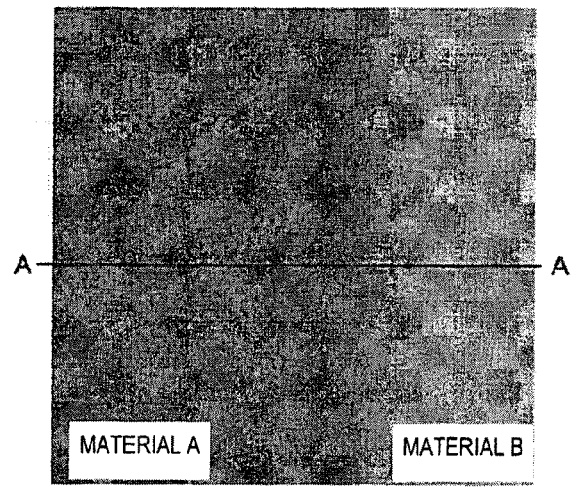
[Fig. 2B]
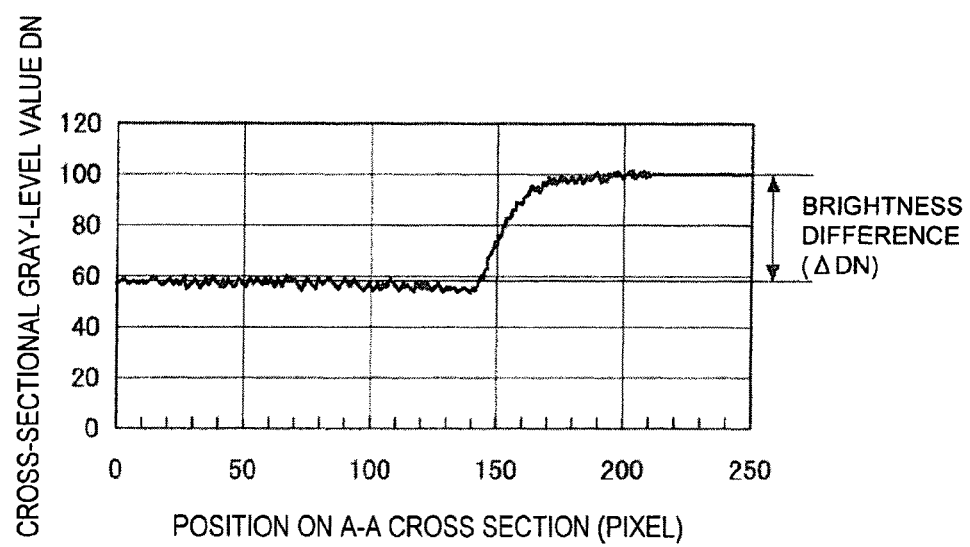

[Fig. 3A]
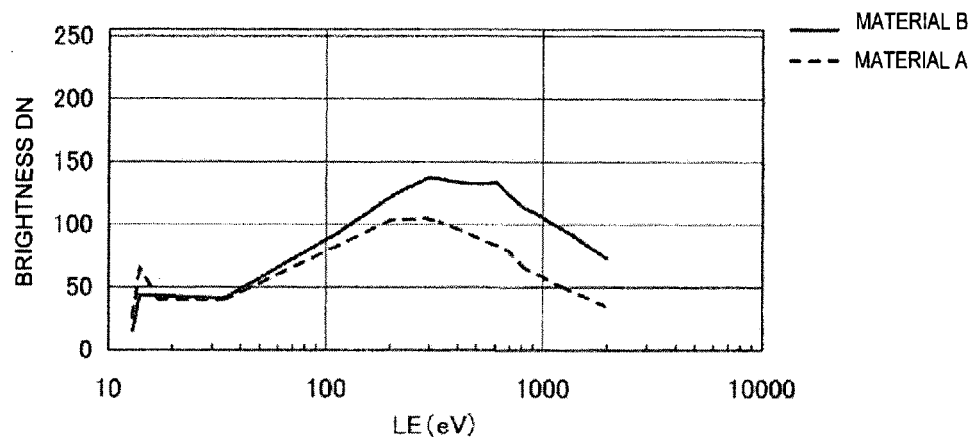
[Fig. 3B]
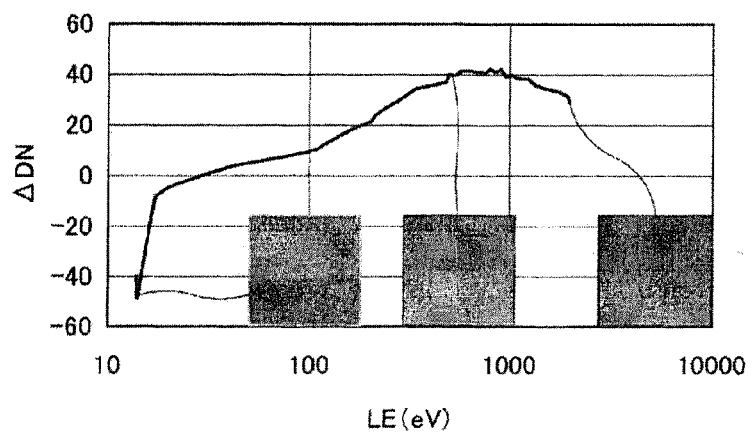
[Fig. 3C]
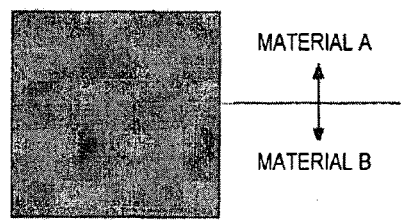

[Fig. 4]
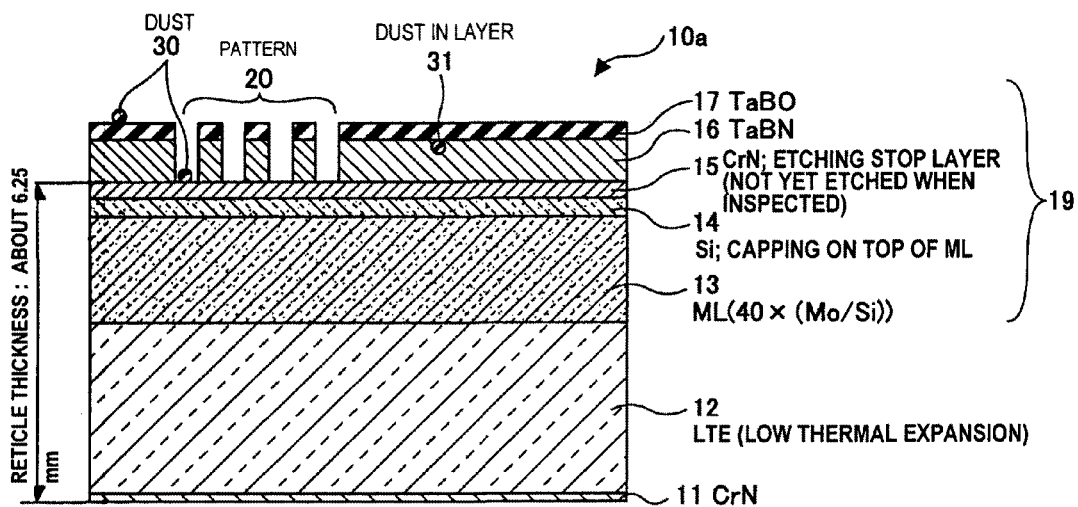
[Fig. 5]
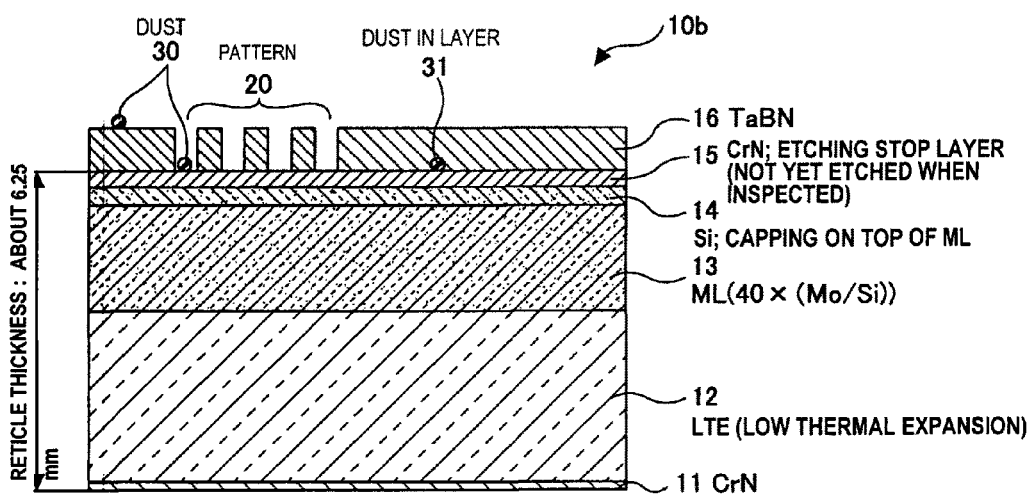

[Fig. 6A]
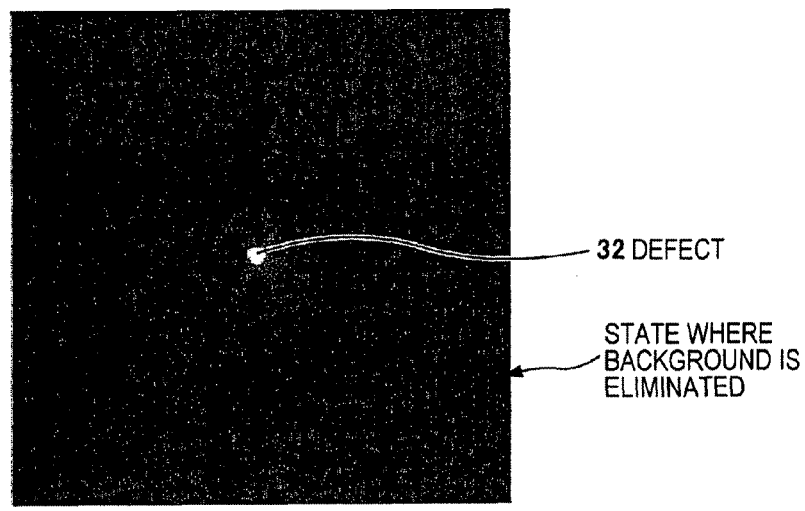
[Fig. 6B]
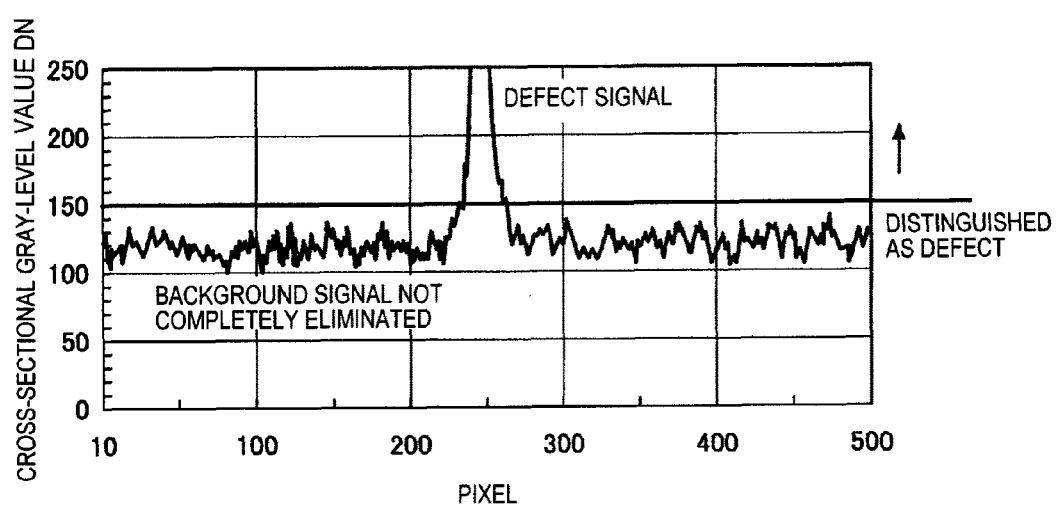

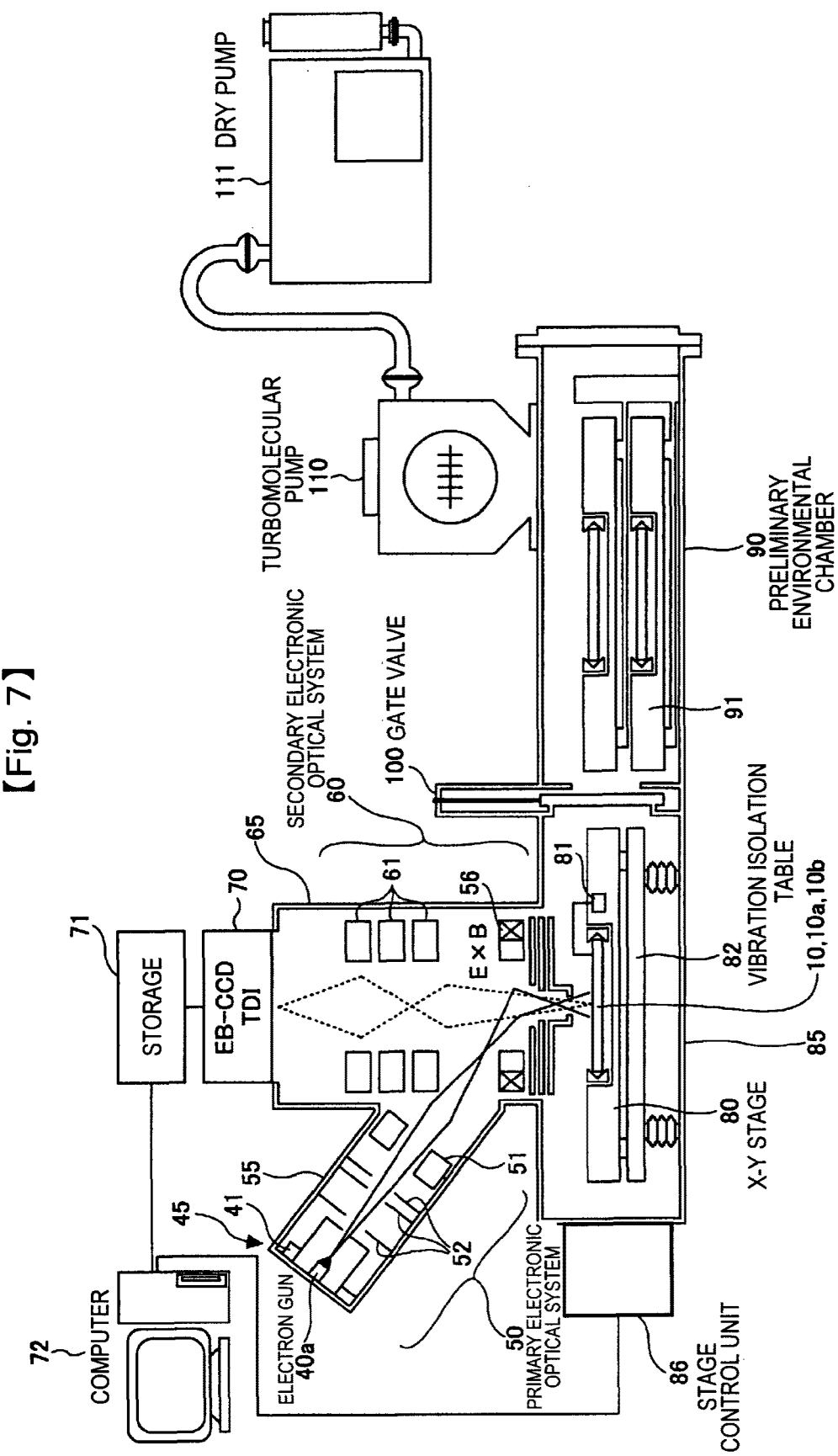
[Fig. 7]

[Fig. 8]
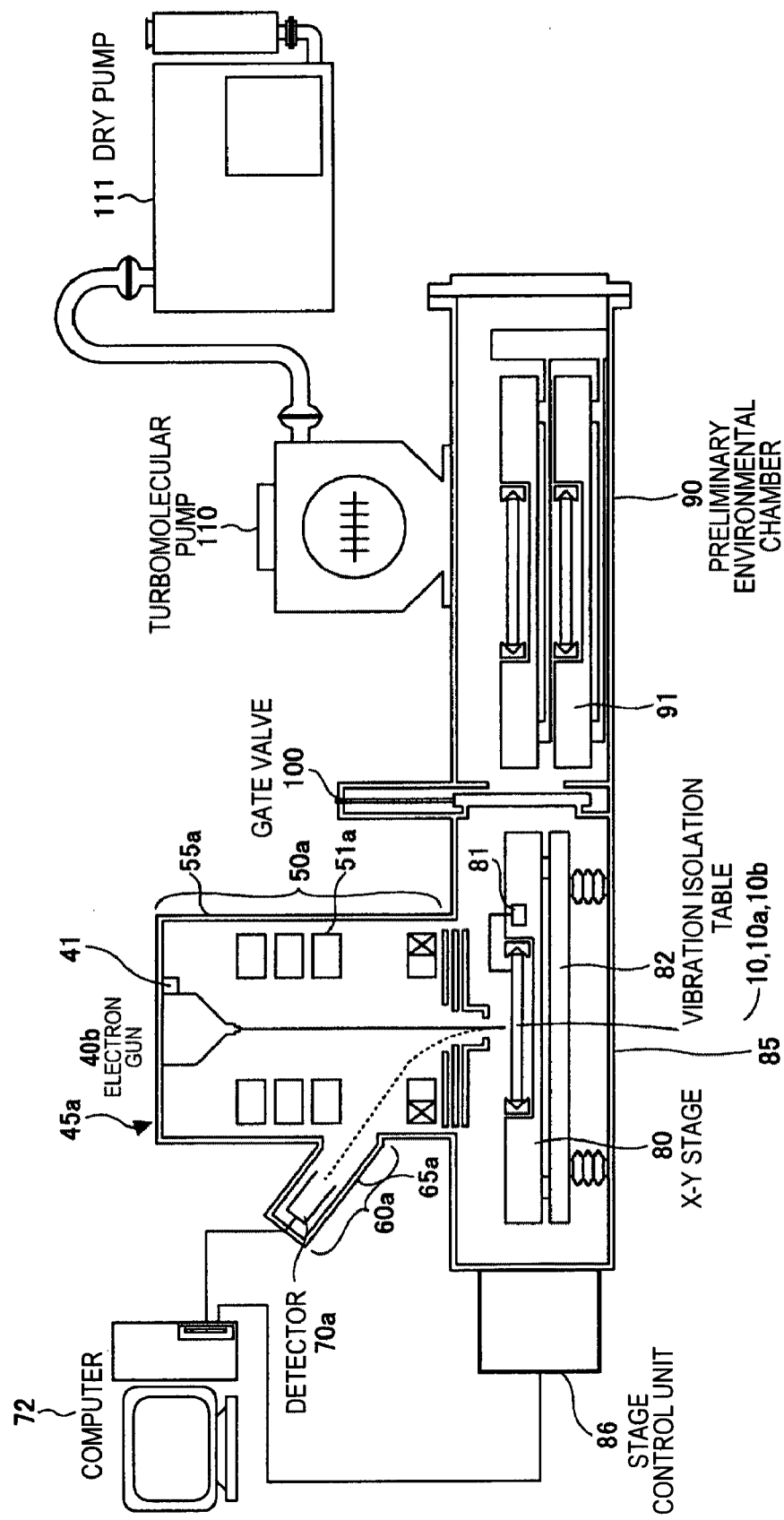

[Fig. 9]
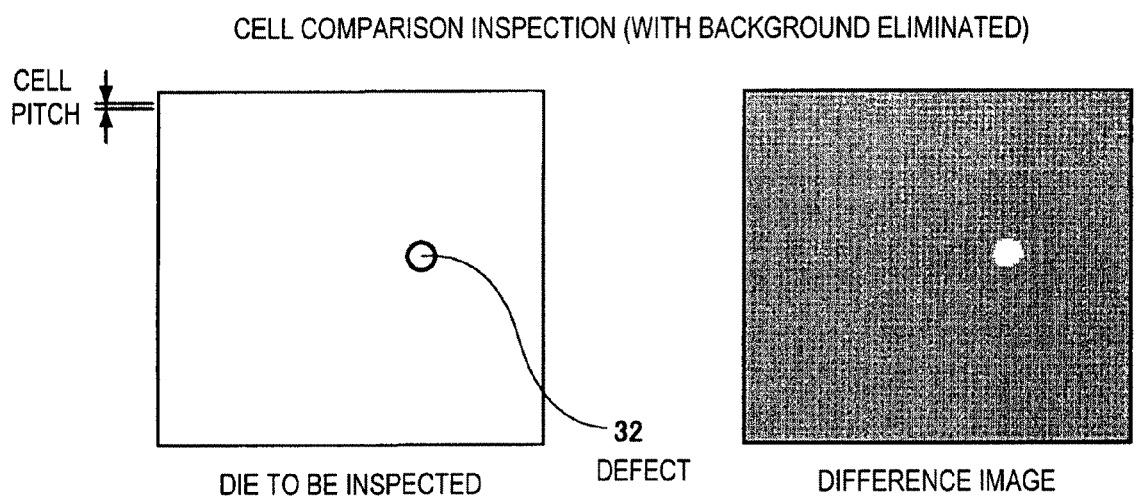

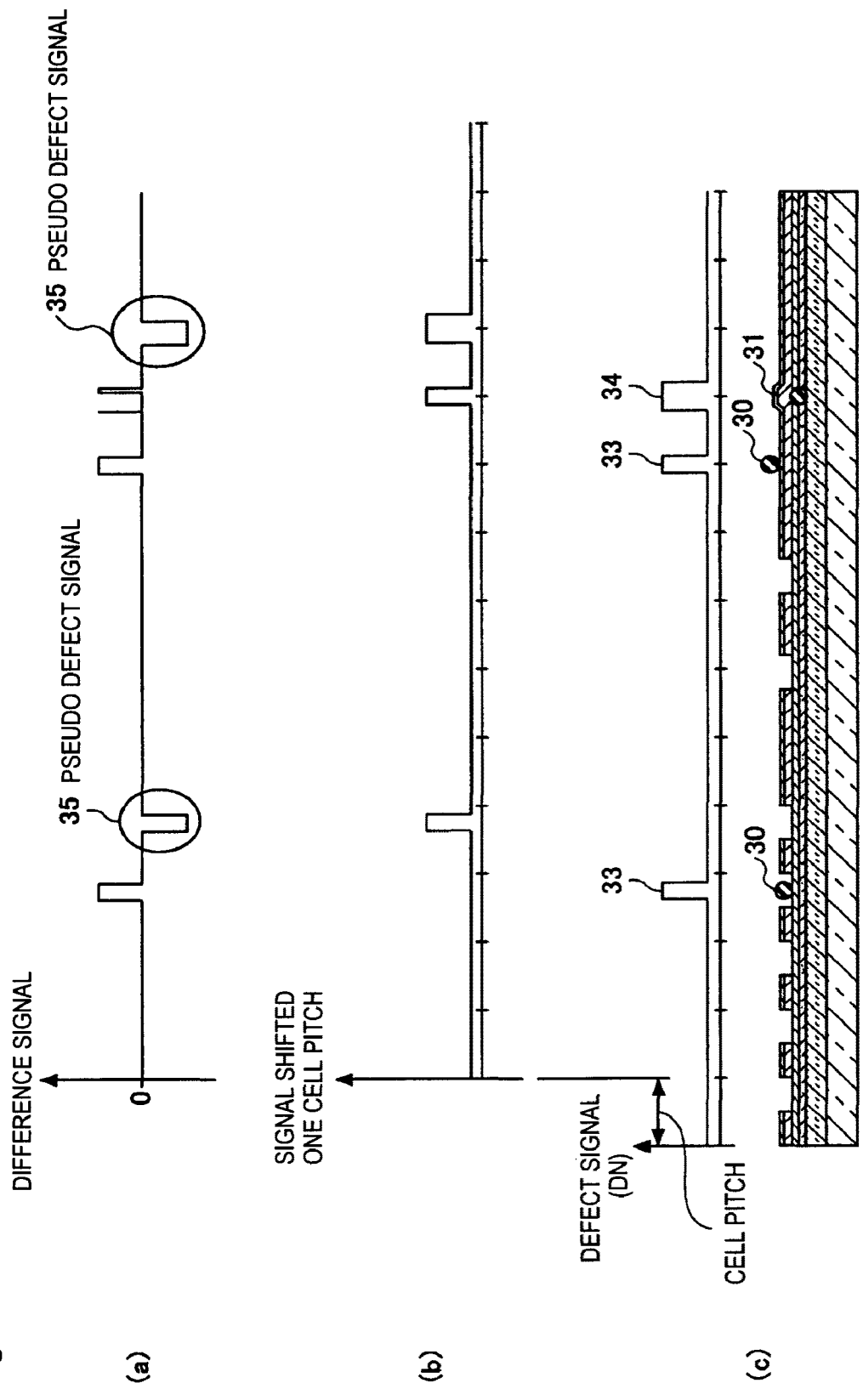

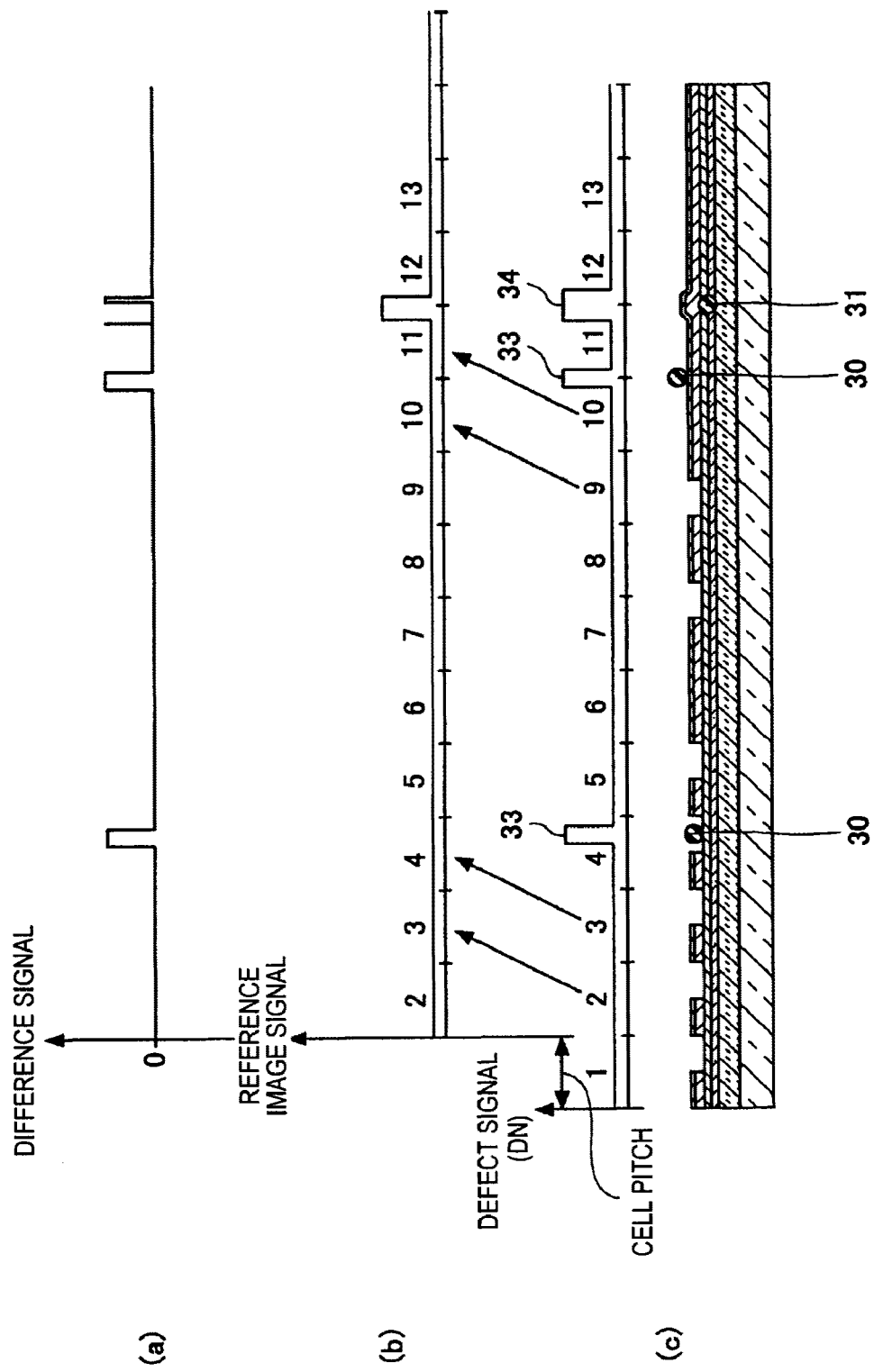

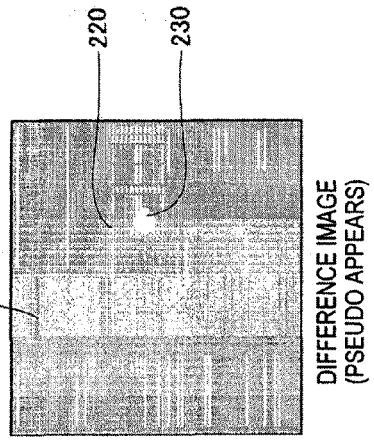
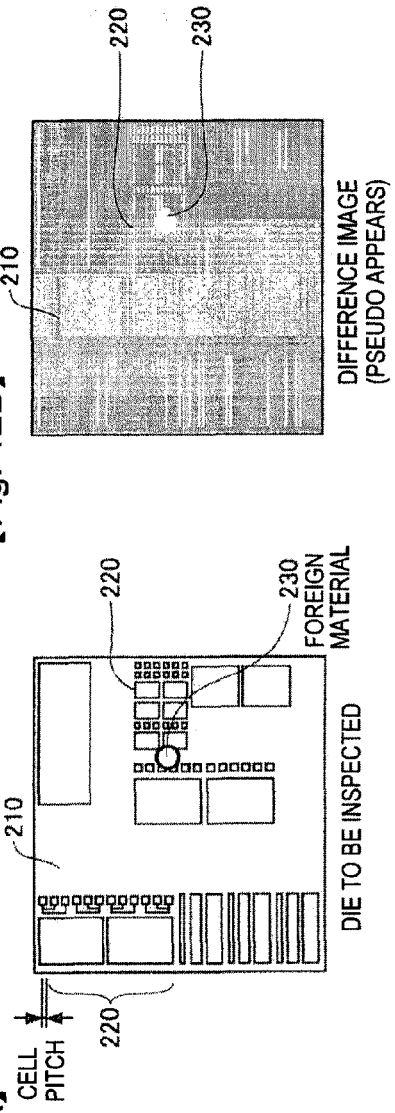
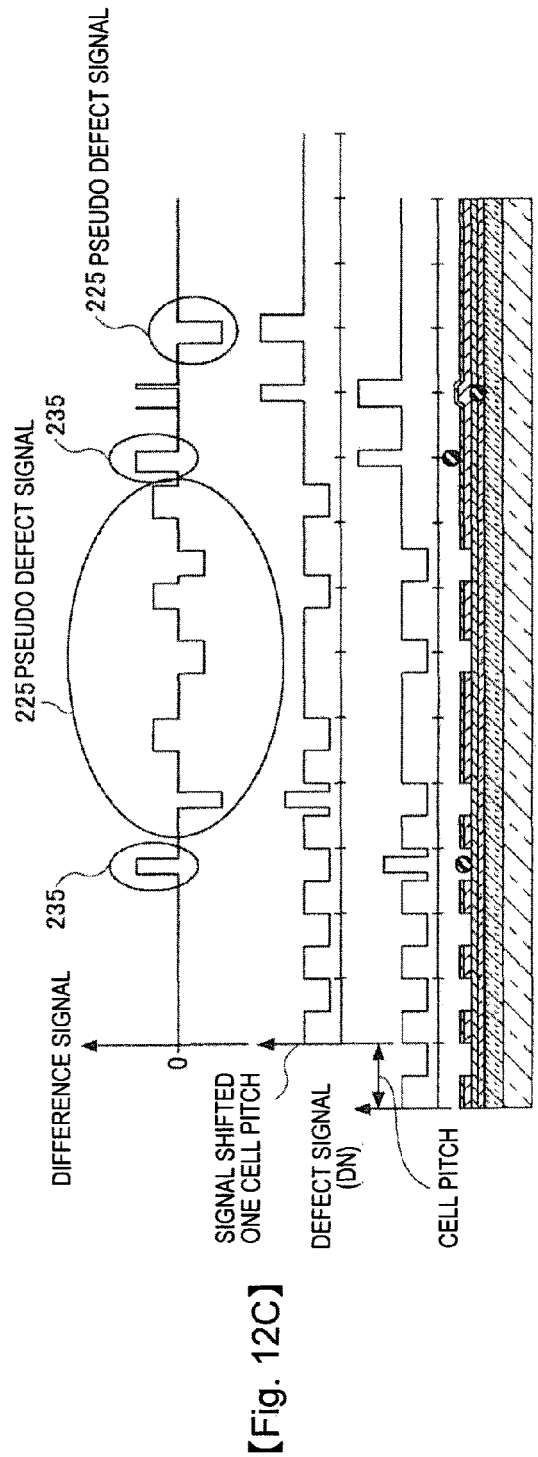

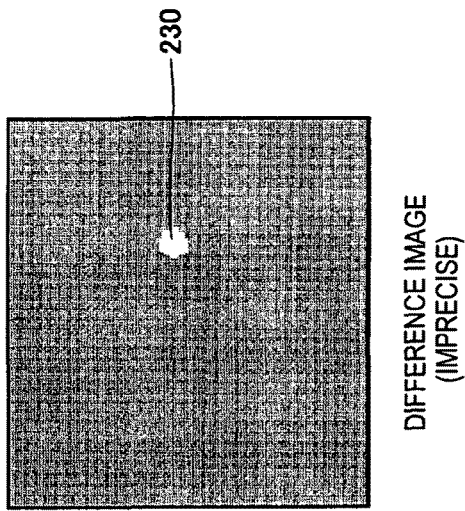
[Fig. 13A] REFERENCE DIE
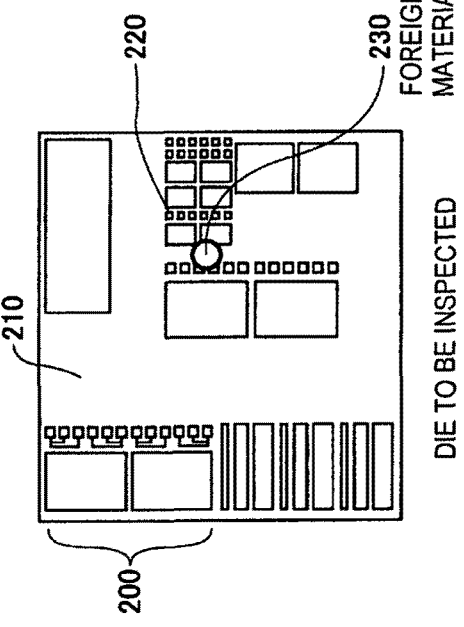
[Fig. 13B] DIE TO BE INSPECTED
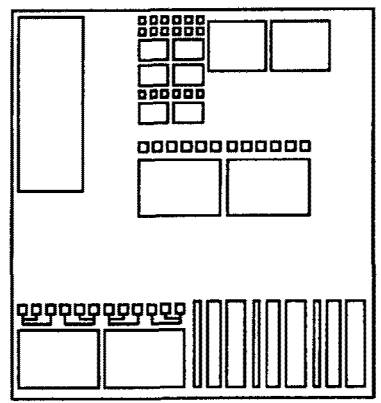
[Fig. 13C] DIFFERENCE IMAGE (IMPRECISE)

SUBSTRATE SURFACE INSPECTION METHOD AND INSPECTION APPARATUS

CROSS REFERENCE TO RELATED APPLICATION

This application claims the benefit of Japanese Patent Application No. 2008-205097 filed on Aug. 8, 2008 in Japan, the subject matter of which is hereby incorporated by reference.

BACKGROUND OF THE INVENTION

1. Field of the Invention

The present invention relates to a substrate surface inspection method and inspection apparatus, and particularly to a substrate surface inspection method and inspection apparatus for detecting a defect on a substrate.

2. Description of the Related Arts

Conventionally, a foreign material inspection method that uses light is known. For example, a conventional foreign material inspection method comprises: irradiating a photomask or other sample with light; receiving light reflected from the sample and light transmitted through the sample to image the sample; and detecting a foreign material by means of a foreign material detection threshold. Such a method is disclosed, for example, in Japanese Patent Laid-Open Application No. 2008-96296.

In the above-described foreign material inspection method, however, the detection limit for a foreign material on a reticle is deemed to be about 50 nm since the method uses light. In recent years, line widths on a reticle have become narrower as pattern sizes of semiconductors have become narrower, so even a small foreign material would be a serious defect. Conventional inspection apparatuses of a light type would have a problem of not being able to detect a foreign material of 50 nm or less in size.

In addition, it would be difficult to distinguish a foreign material on a pattern on a reticle from part of the pattern shape, which would also be a problem. FIGS. 12A to 12C are schematic views of a conventional cell comparison inspection.

FIG. 12A is a schematic view showing one example of a die to be inspected. In FIG. 12A, a pattern 220 including cell areas having a regular pitch is provided on a reticle surface 210. Suppose that the reticle surface 210 is irradiated with an electron beam to be imaged and the presence or absence of a foreign material is inspected for by comparing cells. The cell comparison inspection comprises: acquiring images at a preset cell pitch; comparing those images; and determining from a difference between the images the presence or absence of a defect such as a foreign material 230.

FIG. 12B is a schematic view showing a difference image acquired by the cell inspection. As shown in FIG. 12B here, sections other than a repetitive pattern, i.e. random pattern sections or the like, exist on the image as patterns other than a foreign material (background). Such sections other than a repetitive pattern are all detected as pseudo defects (pseudo foreign materials, in this case).

FIG. 12C shows a principle of the defect detection using the cell comparison. The cell comparison inspection presupposes that patterns repeated at a pitch exist in the inspection area. The minimum unit of the repeated patterns is set as the cell pitch. The defect inspection determines a difference between a signal of a cell on which attention is focused and a signal of the preceding cell. If the difference is zero, one pattern is repeated. If the difference is not zero, there is a shape that is not the minimum unit of the repeated patterns. This shape that is not the repetitive pattern is detected as a defect signal 235.

In a section where a pattern changes or the like, however, there is no repeated-at-a-pitch pattern to be presupposed but there are irregular patterns. The cell pitch cannot be set for such a section, and therefore the difference value of the cell comparison becomes other than zero in a section where a pattern changes or the like. As a result, every such section would be detected as a pseudo defect signal 225, which is the problem.

A die comparison is known as an inspection method for preventing such a problem. FIGS. 13A to 13C are schematic views showing a conventionally used die comparison inspection. FIG. 13A is a schematic view of a reference die, and FIG. 13B is a schematic view of a die to be inspected. FIG. 13C shows a difference image between the reference die and the die to be inspected.

Generally, the die comparison inspection is carried out when a pattern 220 other than a repetitive pattern is inspected for a pattern defect. Since the die size is generally much larger than a cell pitch, the travel of the stage is correspondingly long. For this reason, the positioning accuracy, speed accuracy, rotation angle control accuracy, and the like of the stage are required to be high, that is, the mechanism, control, and the like of the stage are required to be highly precise. The apparatus would therefore be expensive. The image processing algorithm for the image comparison would be complicated, the image processing would correspondingly require time, and the determination of the presence or absence of the foreign material 230 would require a great deal of time.

In contrast to such a die comparison inspection, the cell comparison inspection can accurately carry out an inspection with less cost of the stage mechanism, control algorithm, and the like. The cell comparison inspection also has an advantage of being able to make the inspection time shorter than the die comparison inspection. However, as described above, it is required to solve the problem in which the background interferes when the cell comparison inspection is used to inspect for a foreign material.

SUMMARY OF THE INVENTION

Thus, a purpose of the invention is to provide a substrate surface inspection method and inspection apparatus that can detect defects including a foreign material of 50 nm or less or the like present on a substrate surface easily and precisely by means of the cell inspection.

The invention is a substrate surface inspection method for inspecting for a defect on a substrate including a plurality of materials on a surface thereof, the substrate surface inspection method comprising: irradiating the surface of the substrate with an electron beam, a landing energy of the electron beam set such that a contrast between at least two types of materials of the plurality of materials is within a predetermined range; detecting electrons generated by the substrate to acquire a surface image of the substrate, with a pattern formed thereon from the at least two types of materials eliminated or weakened; and detecting the defect from the acquired surface image by detecting as the defect an object image having a contrast by which the object image can be distinguished from a background image in the surface image.

Another aspect of the invention is a substrate surface inspection apparatus for inspecting for a defect on a substrate including a plurality of materials on a surface thereof, the substrate surface inspection apparatus comprising: an electron gun for irradiating the surface of the substrate with an electron beam, a landing energy of the electron beam set such that a contrast between at least two types of materials of the plurality of materials is within a predetermined range; an imaging device for detecting electrons generated by the substrate to acquire a surface image of the substrate, with a pattern formed thereon from the at least two types of materials eliminated or weakened; and an arithmetic processor for detecting the defect from the acquired surface image by detecting as the defect an object image having a contrast by which the object image can be distinguished from a background image in the surface image.

The invention allows a defect present on a substrate to be detected easily.

As described hereafter, other aspects of the invention exist. Thus, this summary of the invention is intended to provide a few aspects of the invention and is not intended to limit the scope of the invention described and claimed herein.

BRIEF DESCRIPTION OF THE DRAWINGS

The accompanying drawings are incorporated in and constitute a part of this specification. The drawings exemplify certain aspects of the invention and, together with the description, serve to explain some principles of the invention.

FIG. 1 shows a relation of an acceleration voltage Vacc, a retarding voltage RTD, and a landing energy LE to one another in a substrate surface inspection method and inspection apparatus according to a present embodiment;

FIG. 2A shows an example of a difference in brightness of an image between component materials irradiated with an electron beam, and particularly shows an example of an image having a brightness difference between materials A and B;

FIG. 2B shows a relation between a position and a cross-sectional gray-level value in Cross Section A-A in FIG. 2A;

FIG. 3A shows a difference in brightness between the materials A and B versus the landing energy LE, and particularly shows a relation between the landing energy LE and the brightness of each of the materials A and B;

FIG. 3B shows a contrast between the materials A and B;

FIG. 3C shows an example of a surface image acquired with a pattern eliminated;

FIG. 4 shows an example of a structure of a specific reticle;

FIG. 5 shows an example of a cross-sectional structure of a reticle substrate that is different from that in FIG. 4;

FIG. 6A shows a surface image including a defect image, with a background pattern on the substrate surface eliminated;

FIG. 6B shows a cross-sectional gray level of the image in FIG. 6A;

FIG. 7 shows an example of a general configuration of the substrate surface inspection apparatus;

FIG. 8 shows an example of a general configuration of a substrate surface inspection apparatus that is different from that in FIG. 7;

FIG. 9 schematically shows a cell comparison inspection with a background eliminated;

FIG. 10 shows a principle of defect detection using cell comparison with a background on a substrate surface eliminated, where (a) shows difference signals, (b) shows substrate surface signals that are shifted one cell pitch, and (c) shows the substrate surface signals with a cross section of the substrate;

FIG. 11 shows a principle of defect detection using cell comparison with a background eliminated, where (a) shows difference signals, (b) shows reference image signals, and (c) shows defect signals obtained by imaging, with a cross section of the substrate;

FIG. 12A schematically shows a conventional cell comparison inspection, and particularly shows an example of a die to be inspected;

FIG. 12B shows a difference image obtained from the die to be inspected in FIG. 12A;

FIG. 12C, relating to FIGS. 12A and 12B, shows a principle of defect detection using the conventional cell comparison;

FIG. 13A schematically shows a conventional die comparison inspection, and particularly shows a reference die;

FIG. 13B schematically shows a die to be inspected of the conventional die comparison inspection; and FIG. 13C shows a difference image of the conventional die comparison inspection.

DETAILED DESCRIPTION

The following detailed description refers to the accompanying drawings. Although the description includes exemplary implementations, other implementations are possible and changes may be made to the implementations described without departing from the spirit and scope of the invention. The following detailed description and the accompanying drawings do not limit the invention. Instead, the scope of the invention is defined by the appended claims.

The invention is a substrate surface inspection method for inspecting for a defect on a substrate including a plurality of materials on a surface thereof, the substrate surface inspection method comprising: irradiating the surface of the substrate with an electron beam, a landing energy of the electron beam set such that a contrast between at least two types of materials of the plurality of materials is within a predetermined range; detecting electrons generated by the substrate to acquire a surface image of the substrate, with a pattern formed thereon from the at least two types of materials eliminated or weakened; and detecting the defect from the acquired surface image by detecting as the defect an object image having a contrast by which the object image can be distinguished from a background image in the surface image.

The invention allows a surface image to be acquired with a substrate surface pattern eliminated when the substrate is irradiated with an electron beam. When a defect exists on the substrate, a surface image can be obtained in which the defect is in some way isolated from its background image. Defects can therefore be detected easily and precisely. Incidentally, "a pattern eliminated or weakened" means a state where an actual pattern exists on a substrate but the pattern in an image is eliminated or weakened (hereinafter the same shall apply).

The contrast between the background image and the defect may be three times or more the contrast between the at least two types of materials.

This allows the defect to be distinguished from the background image with a sufficient contrast even when a boundary between the two types of materials is not completely eliminated. The defect can therefore be detected easily.

The inspection method of the invention may include a pre-irradiation process before the electron beam irradiation process, where the pre-irradiation process may comprise irradiating at least once with an electron beam whose landing energy is different from that in the electron beam irradiation process.

Consequently, the conditions of the substrate can be adjusted in advance such that the contrast between the two types of materials is lowered, and then the substrate can be irradiated with an electron beam for the inspection. A flexible inspection can thus be carried out appropriately according to characteristics of the materials and substrate.

The pre-irradiation process may comprise irradiating a plurality of times with the electron beam, the landing energy of which may be varied for each of the plurality of times of irradiations.

Consequently, the state of charge of the substrate surface can be adjusted in stages, and then the substrate can be irradiated with the imaging-purpose electron beam. A surface image can thus be acquired with a pattern on the surface appropriately eliminated.

The landing energy of the electron beam of the electron beam irradiation process may be 1 eV or more but not exceeding 50 eV.

This allows the substrate to be irradiated with an electron beam of low landing energy. A pattern on the substrate surface can thus be appropriately eliminated by means of mirror electrons.

The substrate may be a reticle.

This allows a defect on a reticle, which is used for exposure, to be detected easily and precisely.

The defect may include a foreign material.

This allows dust or other foreign materials on the substrate to be detected easily and precisely.

Another aspect of the invention is a substrate surface inspection apparatus for inspecting for a defect on a substrate including a plurality of materials on a surface thereof, the substrate surface inspection apparatus comprising: an electron gun for irradiating the surface of the substrate with an electron beam, a landing energy of the electron beam set such that a contrast between at least two types of materials of the plurality of materials is within a predetermined range; an imaging device for detecting electrons generated by the substrate to acquire a surface image of the substrate, with a pattern formed thereon from the at least two types of materials eliminated or weakened; and an arithmetic processor for detecting the defect from the acquired surface image by detecting as the defect an object image having a contrast by which the object image can be distinguished from a background image in the surface image.

Consequently, a surface image can be acquired in which the defect is displayed as if it is isolated from its uniform background image, and the defect can be detected easily and precisely.

Now, an embodiment of the invention will be described with reference to the drawings.

FIG. 1 shows a relation of an acceleration voltage Vacc, a retarding voltage RTD, and a landing energy LE to one another in a substrate surface inspection method and inspection apparatus according to an embodiment of the invention. In FIG. 1, a substrate 10 for a reticle or other mask is placed, and an electron beam is emitted from an electron gun 40 toward the substrate 10.

The type and use of the substrate 10 may be various. For example, a reticle for exposure may be applied. In a case where a reticle is applied to the substrate 10, the substrate 10 has a glass substrate 12 whose backside is covered with a CrN layer 11, the top side of the glass substrate 12 being laminated with a multilayer comprising a plurality of layers 13 to 16, and the reticle is thus formed. The surface of the substrate 10 is covered with a topmost layer 16 comprising a material B. Under the topmost layer 16 exists a second layer 15 comprising a material A. A pattern 20 is formed on the topmost layer 16. The second layer 15 of the material A is exposed where the pattern 20 is formed. The surface of the substrate 10 is therefore formed of the two types of materials, i.e. the material B forming the topmost layer 16 and the material A forming the exposed second layer 15. As above, a plurality of materials compose the surface of the substrate 10 in a common reticle. As the embodiment, the description given below is of the example in which a reticle is applied to the substrate 10. However, the substrate surface inspection method and inspection apparatus according to the embodiment can be applied to other type of substrate 10, such as a semiconductor wafer and a liquid crystal substrate.

In order to accelerate electrons generated by the electron gun 40 toward the ground, an arbitrary voltage of −4000 V to −7000 V is applied to the electron gun 40, for example. This voltage is called the acceleration voltage (Vacc). Suppose that, for example, −4000 V is applied to the surface of the reticle. The voltage applied to the reticle is called the retarding voltage or substrate voltage (RTD). The voltage of the reticle viewed from the electrons accelerated toward the ground is 0 V when the acceleration voltage is −4000 V, and −3000 V when the acceleration voltage is −7000 V. This voltage of the reticle viewed from the electrons accelerated toward the ground (the voltage of the reticle with respect to the accelerated electrons) is the landing energy LE. That is, the landing energy LE is a value obtained by subtracting the retarding voltage RTD from the acceleration voltage Vacc.

When the landing energy LE is adjusted in steps of about 100 V, the acceleration voltage Vacc is changed. When the adjustment is in steps of about 10 V, the landing energy LE may be adjusted by changing the retarding voltage RTD. Suppose that a voltage other than the retarding voltage RTD is superimposed on the voltage of the topmost surface of the reticle due to charging up or the like (the other voltage is called the surface voltage $\Delta V$). In this case, the correction of the surface voltage $\Delta V$ is performed by adjusting the retarding voltage RTD.

An electron microscope of an SEM type, an electron microscope of a projection type, and the like use an electron beam to image the surface of the reticle. These apparatuses irradiate the surface of the reticle with an electron beam and detect electrons returning from the surface of the reticle. The amount (number) of returning electrons varies depending on the landing energy LE of the emitted electron beam, and also varies depending on the types of materials forming the surface of the reticle. The difference in the amount of electrons shows up in an image as a brightness difference (contrast) based on the difference in materials, and thus an image of the surface of the reticle can be obtained.

FIGS. 2A and 2B show an example of the difference in brightness according to the component materials of the substrate irradiated with an electron beam. FIG. 2A shows an image having a brightness difference between the materials A and B. FIG. 2B shows a relation between a position and a cross-sectional gray-level value (i.e. brightness value) in Cross Section A-A in FIG. 2A. The gray-level value (or gradation value) is the magnitude of brightness in the whole gray-level range, and therefore corresponds to the brightness value.

As shown in FIG. 2A, the brightness differs depending on the difference in the type of material, and thus a surface image having a contrast can be acquired.

FIG. 2B numerically expresses the contrast of the image shown in FIG. 2A. In FIG. 2B, pixel coordinates 170 to 250 are included in the area of the material B, where the cross-sectional gray-level value DN is 100. Pixel coordinates 0 to 140 are included in the area of the material A, where the cross-sectional gray-level value DN is approximately 60. Therefore, the brightness difference $\Delta DN$ (contrast) between the materials A and B is approximately 40. A pattern formed from the materials A and B can be recognized from this brightness difference. Pixel coordinates 140 to 170 form a boundary between the materials A and B.

FIGS. 3A to 3C show a difference in brightness between the materials A and B versus a change in the landing energy LE. FIG. 3A shows a relation between the landing energy LE and the brightness of each of the materials A and B. The landing energy LE is adjusted by controlling the acceleration voltage Vacc.

In FIG. 3A, the brightness of the material A is higher than that of the material B around an area whose landing energy LE ranges from 12 to 17 eV. The brightness of the material A exceeds 50, whereas the brightness of the material B is less than 50. In an area whose landing energy LE ranges approximately from 18 to 35 eV, the brightness of the materials A is almost equal to that of the material B, and is about 45. In the next range where the landing energy LE is higher than about 35 eV, the brightness of the material B becomes higher than that of the material A. The brightness difference reaches its peak (maximum) at a landing energy LE of about 600 to 800 eV. Even when the landing energy LE is 1000 eV or higher, the brightness characteristic remains the same in which the brightness of the material B is higher than that of the material A.

FIG. 3B shows brightness differences (contrasts) calculated by subtracting the brightness of the material A from that of the material B based on the characteristic diagram in FIG. 3A. As can be seen from FIG. 3B, there is a point where the difference in brightness between the materials A and B disappears, i.e. the brightness difference ΔDN=0, as the landing energy LE is changed. In the example in FIG. 3B, the brightness of the material A becomes almost equal to that of the material B around the landing energy LE of 33 eV. In this way, the difference in brightness caused by the difference in the type of material relates to the landing energy LE. By examining in advance this relation between the brightness difference and the landing energy LE, the surface of the reticle can be imaged in a state where there is no brightness difference between the materials A and B.

In such a state, the pattern 20 formed on the reticle is eliminated and not displayed. If there is another material C on the reticle, the material C is distinguished as a part having another new brightness. As a result, only the material C part can be recognized.

FIG. 3C shows an example of a surface image acquired in a state where there is no brightness difference between the materials A and B, the contrast is almost zero, and the pattern is eliminated from the image. If an image can be acquired with a pattern on the surface of the reticle eliminated as shown in FIG. 3C and if a foreign material or other defect having a different brightness exists in the image, the defect can easily be distinguished and the defect detection can easily be carried out.

Suppose that either the material A or the material B exist on the reticle as a defect in a state of a burr for example. In such a case, since the burr part has a contact resistance, the defect can be imaged as another object having the brightness different from that of the material A or the material B.

In general, the cell comparison inspection is carried out particularly when the pattern 20 of the reticle is a repetitive pattern. However, the pattern 20 is not always formed only of a completely identical repetitive pattern. The pattern 20 may include an irregular pattern of a size and shape different from the repetitive pattern. If the cell comparison inspection is applied to a pattern including an irregular pattern, the background pattern may interfere. In contrast to this, if the cell comparison inspection can be carried out with the background pattern eliminated from the image, a precise inspection can be performed. The inspection accuracy can be made higher than the die comparison inspection in which the whole pattern is compared regardless of a repetitive pattern or irregular pattern.

If the relation in FIG. 3B is known in advance as described above, an identical apparatus can have a number of imaging and inspection modes by switching the landing energy LE. When the reticle pattern 20 is to be imaged, observed, and inspected, the inspection apparatus uses the landing energy LE that increases the brightness difference between the materials A and B. When a defect such as a foreign material (e.g. dust comprising the material C) other than the materials A and B is to be detected, the inspection apparatus uses the landing energy LE that eliminates or extremely decreases the brightness difference between the materials A and B.

The embodiment will be described below with reference to a case where the defect is mainly dust or other foreign material. However, the defect includes a defect formed from the material A or B as well as a foreign material formed of the material C totally different from the materials A and B forming the pattern 20 on the surface of the substrate 10. A defect formed from the material A or B is, for example, a burr or other object peeling off from the pattern 20 on the surface. Therefore, in the embodiment, an application example of the foreign material may be an object formed from the same material as a material forming the pattern 20. An object present on the surface of the substrate 10 and stripped off from the pattern 20 may be applied to the embodiment as well as the foreign material. This is because, as described above, these stripped-off objects too have a brightness different from that of the materials forming the pattern 20, and can be distinguished as defects. In the invention, a defect includes all objects that exist on the surface of the substrate 10 but do not form the substrate surface itself, and the like.

FIG. 4 shows an example of a structure of a specific reticle. In FIG. 4, a substrate 10a, i.e. the reticle, has a quartz or other glass substrate 12 whose backside is covered with a CrN layer 11. On the glass substrate 12 is formed a laminated ML layer 13, which comprises molybdenum (Mo) and silicon (Si) and reflects soft X rays (EUV: extreme ultraviolet). A capping layer 14 is provided on the top of the laminated ML layer 13. Above the laminated ML layer 13 and the capping layer 14 is formed a buffer layer 15, which comprises chromium nitride (CrN), ruthenium (Ru), a ruthenium alloy, or the like. On the buffer layer 15 is formed a tantalum boron nitride (TaBN) layer 16 that forms a pattern. Further on the TaBN layer 16 is formed a tantalum boron oxide (TaBO) layer 17 for preventing light reflection during an optical inspection.

The reticle substrate 10a thus has a configuration in which a multilayer 19 is formed on the glass substrate 12, the multilayer 19 comprising the laminated plurality of layers 13 to 17. The pattern 20 is formed on the TaBO layer 17 and TaBN layer 16 composing the surface layer of the multilayer 19. The pattern 20 is provided by etching the surface layer to the depth of the buffer layer 15 where the etching is stopped. In FIG. 4, the surface layer is the TaBO layer 17 and the TaBN layer 16, which are etched to form the pattern 20. The TaBO layer 17 and the buffer layer 15 are exposed on the surface of the reticle substrate 10a. The surface of the reticle substrate 10a therefore comprises the TaBO layer 17 and the buffer layer 15 formed of CrN, that is, the two types of different materials.

Sometimes there is dust or other foreign material 30 in the reticle substrate 10a. The foreign material 30 may exist in the pattern 20, or may exist on the surface of the substrate 10a, i.e. the topmost layer. As shown in the right side of FIG. 4, a foreign material 31 may exist in a layer. The dust or other foreign materials 30 and 31 to become defects thus exist on the topmost surface of the reticle substrate 10a and between laminated layers. Dust on the topmost surface and in a layer would be a fatal defect during pattern transfer. Therefore, dust on a layer or in a layer must be found at stages where each layer is formed and at a stage where the multilayer has been formed to some extent.

As described in FIGS. 3A to 3C, the landing energy LE of the electron beam to be emitted is suitably adjusted to the above-described reticle substrate 10a. The two types of materials forming the surface are TaBO and CrN. So, the landing energy LE is adjusted such that a contrast between TaBO and CrN is within a predetermined range near zero and the pattern 20 is eliminated or weakened. In this way, a surface image in which the foreign material 30 is in some way isolated can be acquired, and therefore the foreign material 30 present on the reticle substrate 10a can be easily detected.

In FIG. 4, there is the foreign material 31 also between the TaBO layer 17 forming the surface layer and the TaBN layer 16. Once the TaBO layer 17 has been formed, an image of the foreign material 31 cannot be obtained simply by irradiating the surface of the substrate 10a with an electron beam. However, the foreign material 31 present on the TaBN layer 16 can be detected, for example, by inspecting the surface of the substrate 10a at a stage where the TaBN layer 16 has been formed. In this case, the landing energy LE of the electron beam is suitably adjusted such that the contrast between the two types of materials, i.e. TaBN and CrN, is within a predetermined range near zero.

FIG. 5 shows an example of a cross-sectional structure of a reticle substrate 10b that is different from that in FIG. 4. Unlike the reticle substrate 10a according to FIG. 4, the reticle substrate 10b in FIG. 5 does not have the TaBO layer 17, which is provided as the topmost layer on the reticle substrate 10a in FIG. 4 for preventing light reflection during an optical inspection. Other components of the reticle substrate 10b are the same as those of the reticle substrate 10a in FIG. 4, and therefore they are given the same reference symbols and will not be described.

In the reticle substrate 10b according to FIG. 5, the topmost layer forming its surface is the TaBN layer 16. The buffer layer 15 of CrN is exposed in an area where the pattern 20 is formed. The exposed part of the buffer layer 15 too forms the surface of the reticle substrate 10b. The surface of the reticle substrate 10b therefore comprises the two different types of materials, i.e. TaBN and CrN. The foreign material 30 exists on the TaBN layer 16, which is the topmost layer of the reticle substrate 10b, or on the buffer layer 15 that is exposed on the surface due to the formation of the pattern 20. For this reason, in the inspection method, the landing energy LE of the electron beam to be emitted to the surface of the reticle substrate 10b is adjusted to cause the brightness difference between TaBN and CrN (i.e. the two materials forming the surface of the reticle substrate 10b) to be a value within a predetermined range near zero in a taken image of the surface. This allows the pattern 20 to be eliminated or weakened, allowing only the foreign material 30 to be an image of a brightness that is different from that of the background image. As a result, the foreign material 30 is displayed such that it can be distinguished from the background image, and consequently the foreign material 30 can be easily detected.

In order to detect the foreign material 31 present in the TaBN layer 16, the substrate surface is suitably inspected at a stage where the buffer layer 15 has been formed. Suppose that the substrate surface is only the buffer layer 15 formed of CrN at the stage where the buffer layer 15 has been formed. In this case, the landing energy LE for irradiating the substrate surface with an electron beam is set such that an image of a brightness with which the foreign material 31 is easily detected can be acquired. On the other hand, if another material is exposed on the substrate surface at the stage where the buffer layer 15 has been formed, the landing energy LE of the electron beam is suitably adjusted such that the contrast between the exposed material and CrN is within a predetermined range near zero. Inspecting with these energy conditions allows the foreign material 31 to be distinguished from the background image and be easily detected.

As described with reference to FIGS. 4 and 5, when the surface of the substrates 10a or 10b comprises at least two types of materials, the landing energy LE of the electron beam to be emitted is adjusted such that the brightness difference between the two types of materials forming the surface is near zero. This allows the foreign materials 30 and 31 present on the surface to be easily detected from the substrates 10a or 10b of various forms.

In the examples described above, the surface of the reticle substrate 10, 10a, or 10b comprises two types of different materials. However, the substrate surface may include three types or more of different materials. In this case, the energy adjustment may be performed such that a pattern of two main materials forming the substrate surface is eliminated. Specifically, the landing energy LE is set such that the contrast between those two types of materials is in a predetermined range. Other conditions may be adjusted for the other materials. For example, images of the other materials may be unfocused and blurred so as not to interfere with the detection of the foreign materials 30 and 31. Practically, the surface of the reticle substrate 10, 10a, or 10b is mostly formed of two types of materials, but if the surface of the reticle substrate includes three types or more of materials, those materials are required not to interfere with the detection of the foreign materials 30 and 31. One appropriate approach is, for example, to blur their images by means of focusing or other optical conditions as described above. In this way, the substrate surface inspection method and inspection apparatus according to the embodiment can also be suitably applied to the substrates 10, 10a, and 10b including three types or more of materials.

FIGS. 6A and 6B show a defect image with a background pattern eliminated and its cross-sectional gray level. FIG. 6A shows a surface image with a background pattern on the substrate surface eliminated, and FIG. 6B shows a cross-sectional gray level of the image in FIG. 6A.

In FIG. 6A, the surface image is acquired in a state where the brightness difference between the two types of materials on the substrate surface is eliminated and the background image is eliminated. As a result, a defect 32 is seen as if it is isolated from the background image, the defect 32 can be distinguished from the background image, and therefore the defect 32 can easily be found.

In FIG. 6B, the horizontal axis represents the pixel coordinate, and the vertical axis represents the cross-sectional gray-level value DN. In the vicinity of a point whose pixel coordinate is 250, the signal of the defect 32 including the foreign material 30 exhibits a high degree of brightness, indicating a gray-level value exceeding 250. On the other hand, at pixel coordinates ranging from 0 to about 220 and from about 270 to 500, the gray-level value of the background signal is not zero but about 100 to 140, and the background pattern is not completely eliminated. In such a case, only the defect 32 can be detected by raising the signal level to be detected as the defect 32 higher than the signal level of the background pattern, as shown in FIG. 6A. If this signal level difference corresponds to, for example, 3 or more in S/N (signal-to-noise ratio), the distinction can easily be made. In the embodiment, if the contrast between the defect 32 and the background image is 2.5 times or more the contrast between the two types of materials forming the substrate surface, or more preferably 3 times or more, the defect 32 can easily be distinguished.

In FIG. 6B, while the background image is not completely eliminated and has a certain degree of brightness difference, the brightness difference between the defect 32 and the background image is large and causes no problem in detecting the defect 32. Therefore, the setting of the landing energy LE of the electron beam can be said to be appropriate. As shown in FIG. 6A, the background pattern is substantially eliminated, so the detection of the defect 32 is easy. Even if some background pattern remains in a weakened manner, the brightness difference between the defect 32 and the background is suitably three times or more the brightness difference between the two types of materials of the substrate surface. Consequently, the weakened background pattern presents no obstacle to the detection of the defect 32. As just described, a weakened background pattern may remain in the embodiment.

Now, an example of the substrate surface inspection apparatus that is applied in order to carry out the inspection method according to the embodiment will be described with reference to FIGS. 7 and 8.

FIG. 7 shows an example of a general configuration of the substrate surface inspection apparatus. In FIG. 7, an electron microscope of a projection type is applied to the inspection apparatus. The inspection apparatus according to the embodiment comprises as main components an electron beam source 45, a primary optical system 50, a secondary optical system 60, an imaging device 70, and a stage 80, and these components are accommodated in vacuum enclosures 55, 65, and 85. The electron beam source 45 generates an electron beam. The primary optical system 50 guides the electron beam to the reticle substrate 10, 10*a*, or 10*b*. Irradiated with the electron beam from the primary optical system 50, the reticle substrate 10, 10*a*, or 10*b* returns electrons. The secondary optical system 60 guides the electrons, returned from the reticle substrate, to the imaging device 70, which captures the returned electrons as an image. The stage 80 is configured to support the reticle substrate 10, 10*a*, or 10*b*, and can move in at least one direction.

The electron beam source 45 uses an electron gun 40*a* of a thermionic emission type. The electron gun 40*a* mainly uses LaB6. Alternatively, the electron gun 40*a* may comprise a filament formed of tungsten, a tungsten-based material such as Th-W and W2C, an oxide cathode formed of (Ba, Sr, Ca)CO3, and the like.

The primary optical system 50 is a means for guiding the electron beam generated by the electron gun 40*a* to the reticle substrate 10, 10*a*, or 10*b*, and comprises an electrostatic lens 51 and an aperture 52.

The electron beam is formed into a circle, an ellipse, or a rectangle by the lens 51 and aperture 52 of the primary optical system 50, and is guided and emitted to the reticle substrate 10, 10*a*, or 10*b*. The electron beam is generally formed in such a way as to have an area or size a little larger than that of the imaging device 70 (TDI, EB-TDI, CCD, EB-CCD, or the like). The size of the electron beam may be adjusted to each imaging device 70. The size of the electron beam may also be set in accordance with the largest imaging device.

The inspection apparatus adjusts the landing energy LE of the electron beam to be emitted to the reticle substrate 10, 10*a*, or 10*b*. The landing energy LE is adjusted by controlling the combination of the acceleration voltage Vacc and the substrate voltage (retarding voltage) RTD. The acceleration voltage Vacc accelerates the electron beam in the primary optical system 50, giving it an arbitrary amount of energy. The acceleration voltage Vacc may be set, for example, by an acceleration voltage setting unit (means) 41. The substrate voltage RTD may be set, for example, by a substrate voltage adjustment mechanism 81 provided on the stage 80. The combination of the acceleration voltage Vacc and the substrate voltage RTD can be changed for information to be obtained from the reticle substrate 10, 10*a*, or 10*b*.

When irradiated with the electron beam, the reticle substrate 10, 10*a*, or 10*b* generates secondary electrons, reflected electrons, and mirror electrons. The reflected electrons are electrons generated by perfectly elastic collision between the emitted electrons and the component materials of the reticle substrate 10, 10*a*, or 10*b*. The mirror electrons are electrons rebounding from the proximity of the surface of the reticle substrate 10, 10*a*, or 10*b* when the electron beam is emitted, that is, the mirror electrons are electrons rebounding without colliding with the substrate. The mirror electrons are generated by the effect of the surface potential caused by charging of the reticle substrate 10, 10*a*, or 10*b*. For example, when a secondary electron image of the reticle substrate 10, 10*a*, or 10*b* is to be obtained, the acceleration voltage Vacc is set between 100 eV and a few kilo electron volts. The substrate voltage RTD is set to a setup voltage for the secondary system (a condition for electrons to travel straight through an ExB filter 56 functioning as the secondary system). When a reflected electron image is to be obtained, the substrate voltage RTD is adjusted. When an image of the mirror electrons is to be obtained, the landing energy LE is set between zero and tens of electron volts.

By changing the acceleration voltage Vacc and the substrate voltage RTD, the above-described configuration can provide the relation between the landing energy LE and the brightness difference as shown in FIGS. 3A and 3B.

The stage 80 is a support table for supporting the reticle substrate 10, 10*a*, or 10*b*, and can move at least in a horizontal direction. The stage 80 is supported on a vibration isolation table 82, which prevents vibration from being transmitted from the floor to the stage 80. The operation of the stage 80 is controlled by an external stage control unit 86. On the stage 80 is provided the substrate voltage adjustment mechanism 81 that sets the substrate voltage RTD as described above, allowing the substrate voltage RTD to be adjusted. The landing energy LE of the electron beam is set in accordance with the substrate voltage RTD and the acceleration voltage Vacc.

The secondary optical system 60 comprises a plurality of electrostatic lenses 61. In the specific embodiment shown in FIG. 7, the primary optical system 50 is oblique to the secondary optical system 60. The electron beam emitted from the electron gun 40*a* travels through the ExB filter 56 formed of an electric field and magnetic field, and is applied perpendicularly or almost perpendicularly to the reticle substrate 10, 10*a*, or 10*b*. The electrons generated by the reticle substrate 10, 10*a*, or 10*b* travel straight through the ExB filter 56 in the secondary optical system 60, and are guided to the imaging device 70. The ExB filter 56 is included in both the primary optical system 50 and the secondary optical system 60.

The imaging device (means) 70 can perform scanning imaging by means of TDI (time delay integration). An MCP, a fluorescent screen, an FOP, and the like are provided in front of the TDI. The MCP (micro-channel plate) amplifies the electrons; the fluorescent screen converts the amplified electrons to light, and the FOP (fiber optic plate) guides the light to the TDI. An EB-TDI may be used instead of the TDI. The EB-TDI can directly receive the electrons and convert to an image. When a still image other than a scan image is to be taken, a CCD (charge coupled device) may be used instead of the TDI, and an EB-CCD may be used instead of the EB-TDI. In addition, an EB-CCD may be provided in front of the TDI so that the TDI is used for a scan image and the EB-CCD is used for a still image. The imaging device 70 has a plurality of pixels, which form a detection surface. The electrons generated by the substrate surface are simultaneously detected by the plurality of pixels, and information on the surface (i.e. the area) is thus detected and converted to an image. Various imaging devices 70 having the above-described functions can be applied to the embodiment.

The imaging device 70 is connected to a storage 71, which is connected to a computer, i.e. an arithmetic processor (processing means) 72. The arithmetic processor 72 is connected to the stage control unit 86.

The storage (storage means) 71 is a means for storing the surface image of the reticle substrate 10, 10a, or 10b obtained by the imaging device 70. The surface image stored in the storage 71 is sent to the arithmetic processor 72. The arithmetic processor 72 performs an arithmetic process for detecting the defect 32 including the foreign material 30. The surface image is obtained with the pattern on the substrate surface eliminated or weakened. Using the above surface image, the arithmetic processor 72 performs a defect detection process. Specifically, if the surface image includes an object being different in contrast from the surroundings and having a brightness with which it can be distinguished from the background image, the arithmetic processor 72 determines that such a distinguishable object is the defect 32. As described above, if the contrast between the background image and the defect 32 is 2.5 times or more, 3 times or more, or the like the contrast of the background image, the pattern on the surface in the background image need not completely disappear, and the defect 32 can be distinguished and detected. When the background image pattern (the pattern on the surface image formed of the two types of materials corresponding to the background image) is not completely eliminated but is weakened and remains, there are two brightness values in the background image, and therefore the brightness of the background image cannot be determined uniquely. In this case, either of the two brightness values may be used as a reference of the contrast to calculate the contrast and perform the defect detection process. For example, the brightness of an image (material) whose brightness difference with the defect 32 is smaller may be used as the contrast calculation reference. Alternatively, an average of the two brightness values may be determined as the brightness of the background image (the contrast calculation reference).

Based on the result of the operation of the arithmetic processor 72, the stage control unit 86 controls the drive of the stage 80 to cause the inspection apparatus to inspect the reticle substrate 10, 10a, or 10b at an appropriate position.

A preliminary environmental chamber 90 is arranged adjacent to the vacuum enclosure 85 for accommodating the stage 80. The preliminary environmental chamber 90 can be communicatively connected to the vacuum enclosure 85 by opening and closing a gate valve 100. The preliminary environmental chamber 90 is provided with a temporary storage place 91 where the reticle substrate 10, 10a, or 10b is to stand by before and after an inspection. The preliminary environmental chamber 90 is also provided with a turbomolecular pump 110 and a dry pump 111 that are able to evacuate, and is configured to be able to evacuate the vacuum enclosures 55, 65, and 85 and the preliminary environmental chamber 90. The turbomolecular pump 110 and the dry pump 111 may be additionally provided for each of the vacuum enclosures 55, 65, and 85 as required.

In FIG. 7, the substrate surface inspection method is realized by using an electron microscope of a projection type. This type of microscope need not narrow the electron beam, and can image the surface of the reticle substrate 10, 10a, or 10b without raising the landing energy LE. That is, the inspection apparatus in FIG. 7 can use an electron beam of a low landing energy to cause the reticle substrate 10, 10a, or 10b to generate mirror electrons easily, providing an image of the mirror electrons. The mirror electrons are electrons generated by the electron beam being reflected in front of the reticle substrate 10, 10a, or 10b without colliding therewith. Now, the brightness of the material A would be equal to that of the material B at a landing energy LE of 33 eV in FIG. 3B described above. On the other hand, the mirror electrons are easily generated at a landing energy LE ranging from −10 eV to 50 eV, or more preferably from 1 eV to 50 eV. Therefore, the range in which the mirror electrons are easily generated corresponds to a landing energy band in which the substrate surface inspection method according to the embodiment is easily carried out. As stated above, the inspection apparatus in FIG. 7 can be realized with an electron microscope of a projection type and can image the surface of the reticle substrate 10, 10a, or 10b even at a landing energy LE of 50 eV or less. Consequently, the inspection apparatus in FIG. 7 can be suitably applied to the substrate surface inspection method according to the embodiment.

FIG. 8 shows an example of a general configuration of a substrate surface inspection apparatus that is different from that in FIG. 7. The inspection apparatus in FIG. 8 has a configuration to which an electron microscope of an SEM type is applied.

In FIG. 8, the substrate surface inspection apparatus comprises an electron beam source 45a, a primary optical system 50a, an imaging device 70a, and a stage 80, and these components are contained in vacuum enclosures 55a, 65a, and 85. The electron beam source 45a generates an electron beam. The primary optical system 50a guides the generated electron beam to the reticle substrate 10, 10a, or 10b, and scans with the electron beam. Scanned and irradiated with the electron beam, the reticle substrate 10, 10a, or 10b returns electrons. The imaging device 70a captures the electrons returned from the reticle substrate 10, 10a, or 10b as an image. The stage 80 is configured to support the reticle substrate 10, 10a, or 10b, and can move in at least one direction.

The electron beam source 45a uses an electron gun 40b of a thermionic emission type. The electron gun 40b mainly uses LaB6. Alternatively, the electron gun 40b may comprise a filament formed of tungsten, a tungsten-based material such as Th-W and W2C, an oxide cathode formed of (Ba, Sr, Ca)CO3, and the like.

The primary optical system 50a comprises a plurality of electrostatic lenses and/or electromagnetic lenses 51a.

A secondary electron multiplier is mainly used for the imaging device 70a.

The electron beam is narrowed by the primary optical system 50a, and an image is obtained by scanning with the narrowed electron beam. More specifically, the inspection apparatus irradiates and scans the reticle substrate 10, 10a, or 10b with the electron beam equating to one pixel of the image. The imaging device 70a acquires electrons generated by the reticle substrate 10, 10a, or 10b. Eventually, the whole inspection area on the reticle substrate 10, 10a, or 10b is scanned with the electron beam, the arithmetic processing means 72 completes the surface image of the whole inspection area, and this surface image is used for the detection inspection for the defect 32.

As described above, the substrate surface inspection method according to the embodiment may be carried out, for example, by the substrate surface inspection apparatus to which the electron microscope of an SEM type in FIG. 8 is applied.

Other components than those described above are the same as those of the substrate surface inspection apparatus in FIG. 7, and those components are given the same reference symbols and will not be described.

FIG. 9 schematically shows a cell comparison inspection with a background eliminated. As previously described, the electron beam irradiation condition (the landing energy LE) under which the background is eliminated is determined in advance. This allows the cell comparison inspection to detect the foreign material 30 or the like on the reticle substrate 10, 10a, or 10b to carry out the inspection for the presence or absence of the defect 32.

FIG. 10 shows a principle of defect detection with a background pattern on a substrate surface eliminated. The arithmetic processor 72 performs the defect detection using cell comparison here. In FIG. 10, (c) shows substrate surface signals to be inspected with the background eliminated, with a cross section of the substrate; (b) shows substrate surface signals that are shifted one cell pitch; and (a) shows difference signals between the substrate surface signals that are shifted one cell pitch from each other.

Since the pattern is eliminated as shown in (c) in FIG. 10 in the substrate surface inspection method according to the embodiment, a flat surface (area) continues in the image regardless of the actual pattern. Therefore, the cell comparison inspection can be carried out over the whole area.

In FIG. 10, the signals in (b) are shifted one cell pitch from the acquired defect signals 33 and 34 in (c) in order to carry out the cell comparison inspection. The signal waveform in (b) is simply shifted one pitch from that in (c).

Suppose that, as shown in (a) in FIG. 10, a difference signal is simply determined from a current signal in (c) on which attention is focused and from a signal of the preceding cell in (b). In this case, a signal with a defect and a signal without a defect are compared twice for one defect. As a result, a pseudo defect signal 35 is generated as illustrated.

In order to prevent the above-described pseudo defect signals, the substrate surface inspection method according to the embodiment performs the defect detection using, for example, an algorithm shown in FIG. 11.

FIG. 11 shows a principle of defect detection with a background pattern on the substrate surface image eliminated. A defect is detected by using cell comparison also in this case, and specifically signals of three cells are compared in the process in FIG. 11. In FIG. 11, (c) shows defect signals acquired by imaging, with a cross section of the substrate; (b) shows reference image signals; and (a) shows difference signals acquired eventually.

The algorithm shown in FIG. 11 is constructed to minimize the number of pseudo defects 35 observed in (a) in FIG. 10. This algorithm first compares signals of three cells and, based on a majority decision, chooses signals of two cells closest among the three to be a comparison signal (a reference signal). Then, the algorithm determines a difference between the signal of the cell to be inspected (the focused cell) and the comparison signal. If the difference value is zero, the algorithm determines that there is no defect. On the other hand, if the difference value is not zero, the algorithm detects the inspected part as a defect.

In FIG. 11, the surface image signals in (c) include two defect signals 33 corresponding to the two foreign materials 30, and one defect signal 34 which is due to the foreign material 31 present in a layer. In the inspection process, the imaged surface image signals (c) are first processed to create the reference image signals (b) to be compared with the surface image signals (c). One reference image signal (b) is created here based on a majority decision from signals of three cells of the surface image signals (c). For example, suppose that a reference image signal for one focused cell is created by comparing its signal with signals of the preceding two cells. Cell 3 is compared with Cells 1 and 2. Signals of Cells 1 and 2 are both the same as that of Cell 3 on which attention is focused. So, the signal of Cell 2 is chosen to be the reference image signal for Cell 3 in (b). Attention is then focused on Cell 4 in (c). Cell 4 is compared with the preceding two cells, i.e. Cells 2 and 3. The defect signal 33 of Cell 4 is a signal indicating the foreign material 30. Signals of Cells 2 and 3 are obtained in a state where there is no defect, and are equal to each other. So, based on a majority decision, the signal of Cell 3 is chosen to be the reference image signal for Cell 4 in (b). Similarly, attention is focused on Cell 10 in (c). Cell 10 is compared with Cells 8 and 9. Signals of Cells 8 and 9 are obtained in a state where there is no foreign material 30. Accordingly, the signal of Cell 9 is chosen to be the reference image signal for Cell 10. Cell 11 is compared with Cells 9 and 10. In this case, the signal of Cell 9 is a defect-free signal obtained with no foreign material 30. On the other hand, signals of Cells 10 and 11 correspond to the defect signals 33 and 34 obtained with the foreign materials 30 and 31 being present. Accordingly, based on a majority decision, the defect signal of Cell 10 in the imaged signals is chosen and used as the reference image signal for Cell 11.

In this way, the reference image signals in (b) in FIG. 11 are created based on a majority decision among three consecutive cells. Then in the inspection process, the reference image signals in (b) are subtracted from the imaged defect signals in (c) to determine the differences. This provides the difference signals as shown in (a) in FIG. 11. Certainly, the defects 32 caused by the foreign materials 30 and 31 in the cross section of the substrate shown in (c) in FIG. 11 are accurately detected in the difference signals.

As described above, the defects caused by the foreign materials 30 and 31 can be detected easily and precisely by using the algorithm shown in FIG. 11.

Substrate surface inspections according to the embodiment include an inspection for a pattern defect and an inspection for the presence or absence of the defect 32 on the reticle substrate 10, 10a, or 10b. Each of the inspections can be carried out with a landing energy LE suited to each inspection. The electron beam irradiation can be performed a plurality of times in order to efficiently carry out the inspections for the presence or absence of the defect 32 and for a pattern defect. The landing energy LE of the electron beam may be varied for each of the plurality of times of electron beam irradiations.

The inspection for the presence or absence of the defect 32 may include irradiating a plurality of times with the electron beam. The landing energy LE of the electron beam may be varied for each of the plurality of times of irradiations. The application of a combination of different landing energies LE can improve the signal intensity of the defect 32, and also can completely eliminate the background pattern.

In a case where the irradiation is performed twice, an electron beam of a little high landing energy LE (e.g. 28 eV) may be emitted first, and then (secondly) an electron beam of a landing energy LE lower than that in the first time (e.g. 15 eV) may be emitted. This can improve the signal intensity of the defect 32.

The above-described electron beam irradiation at a stage before imaging is called pre-irradiation. In a suitable embodiment, the pre-irradiation process comprises irradiating at least once with an electron beam whose landing energy is different from that of the electron beam for imaging. Consequently, the conditions of the substrate can be adjusted in advance such that the contrast between the two types of materials is lowered, and then the substrate can be irradiated with the electron beam for the inspection. A flexible inspection can thus be carried out appropriately according to characteristics of the materials and substrate.

The pre-irradiation process may comprise irradiating a plurality of times with the electron beam. The landing energy of the electron beam may be different between or varied for each of the plurality of times of pre-irradiations. Consequently, the state of charge of the substrate surface can be adjusted in stages, and then the substrate can be irradiated with the imaging-purpose electron beam. A surface image can thus be acquired with the pattern on the surface appropriately eliminated.

The setting of the secondary optical system (the position of the NA (not shown) ) may be displaced from its regular position. This offset can improve the signal intensity of the foreign material 30.

As described above, the change of the landing energy LE and the fine adjustment of the secondary optical system, the NA position (not shown) can eliminate the background to improve the signal intensity of the defect 32, so that the presence or absence of a smaller defect 32 can be inspected for.

Variations of the embodiment will be described. In the embodiment, an example has been described in which the invention is applied to detecting defects of the surface of the reticle substrate 10, 10a, or 10b. However, the invention can also be applied to a semiconductor wafer and other substrates, including the above-described pattern defect inspection and defect inspection.

The invention can also be applied suitably even when three types or more of materials are included on the surface of the substrate 10, 10a, or 10b. In this case, the pattern may be eliminated for two types of materials that make up the major portion. Specifically, the landing energy LE is set such that the contrast between those two types of materials is in a predetermined range. Focusing or other optical conditions and other conditions may be suitably adjusted so that the other materials do not interfere with the detection of the defect 32 including the foreign materials 30 and 31. Consequently, the invention can also be suitably applied when the substrate surface comprises three types or more of materials.

Within the scope of the invention, another configuration is conceivable for the case where the substrate surface includes three types or more of materials. There may be various material combinations that form the substrate surface. Therefore, the landing energy LE may be able to be set such that the contrast among the three types or more of materials is lowered to within a predetermined range, based on the principle in FIG. 3B. In such a case, the landing energy LE may be adjusted to such an appropriate value to eliminate the pattern of the three types or more of materials.

Persons of ordinary skill in the art will realize that many modifications and variations of the above embodiments may be made without departing from the novel and advantageous features of the present invention. Accordingly, all such modifications and variations are intended to be included within the scope of the appended claims. The specification and examples are only exemplary. The following claims define the true scope and spirit of the invention.

What is claimed is:

1. A method for inspecting for a defect on a substrate including a plurality of materials on a surface thereof, the method comprising:
    setting a landing energy of an electron beam based on at least two type of materials of the plurality of materials so that a pattern formed on the surface image of the substrate from the at least two types of materials can be eliminated or weakened;
    irradiating the surface of the substrate with electron beam;
    detecting electrons generated by the substrate to acquire a surface image of the substrate; and
    detecting the defect from the acquired surface image by detecting as the defect an object image having a contrast by which the object image can be distinguished from a background image which is consisted of the eliminated of weakened image of two types of materials.

2. The method according to claim 1, wherein the contrast between the background image and the defect is three times or more the contrast between the at least two types of materials.

3. The method according to claim 1, including a pre-irradiation process before the electron beam irradiation process, wherein the pre-irradiation process comprises irradiating at least once with an electron beam whose landing energy is different from that in the electron beam irradiation process.

4. The method according to claim 3, wherein the pre-irradiation process comprises irradiating a plurality of times with the electron beam, the landing energy of which is varied for the plurality of times of irradiations.

5. The method according to claim 1, wherein the landing energy of the electron beam of the electron beam irradiation process is 1 eV or more but not exceeding 50 eV.

6. The method according to claim 1, wherein the substrate is a reticle.

7. The method according to claim 1, wherein the defect includes a foreign material.

8. An apparatus for inspecting for a defect on a substrate including a plurality of materials on a surface thereof, the substrate surface inspection apparatus comprising:
    an electron gun for irradiating the surface of the substrate with an electron beam wherein a landing energy of the electron beam is set so that a pattern formed on the surface image of the substrate from the at least two types of materials can be eliminated or weakened;
    an imaging device for detecting electrons generated by the substrate to acquire a surface image of the substrate; and
    an arithmetic processor for detecting the defect from the acquired surface image by detecting as the defect an object image having a contrast by which the object image can be distinguished from a background image which is consisted of the eliminated or weakened image of two types of materials.

* * * * *